US011732031B2

(12) United States Patent
Takahashi et al.

(10) Patent No.: US 11,732,031 B2
(45) Date of Patent: Aug. 22, 2023

(54) METHOD FOR PRODUCING INFLUENZA HA SPLIT VACCINE

(71) Applicant: JAPAN as represented by DIRECTOR GENERAL of National Institute of Infectious Diseases, Tokyo (JP)

(72) Inventors: Yoshimasa Takahashi, Tokyo (JP); Yu Adachi, Tokyo (JP); Manabu Ato, Tokyo (JP)

(73) Assignee: JAPAN as represented by DIRECTOR GENERAL of National Institute of Infectious Diseases, Tokyo (JP)

( * ) Notice: Subject to any disclaimer, the term of this patent is extended or adjusted under 35 U.S.C. 154(b) by 0 days.

(21) Appl. No.: 16/292,065

(22) Filed: Mar. 4, 2019

(65) Prior Publication Data

US 2019/0345231 A1   Nov. 14, 2019

Related U.S. Application Data

(63) Continuation-in-part of application No. PCT/JP2018/032537, filed on Sep. 3, 2018.

(30) Foreign Application Priority Data

Sep. 4, 2017   (JP) .................. 2017-169230
Jul. 23, 2018  (JP) .................. 2018-137952

(51) Int. Cl.
| C07K 1/113 | (2006.01) |
| A61K 39/42 | (2006.01) |
| C07K 16/10 | (2006.01) |

(52) U.S. Cl.
CPC .......... *C07K 16/1018* (2013.01); *A61K 39/42* (2013.01); *C07K 1/113* (2013.01)

(58) Field of Classification Search
None
See application file for complete search history.

(56) References Cited

U.S. PATENT DOCUMENTS

| 2010/0099870 A1 | 4/2010 | Isobe et al. |
| 2012/0270255 A1 | 10/2012 | Graninger et al. |
| 2015/0098966 A1 | 4/2015 | Ni et al. |
| 2016/0045590 A1 | 2/2016 | Milner et al. |
| 2016/0052997 A1 | 2/2016 | Hong et al. |
| 2019/0142930 A1 | 5/2019 | Ni et al. |
| 2021/0353737 A1 | 11/2021 | Takahashi et al. |

FOREIGN PATENT DOCUMENTS

| JP | 2018-501801 | 1/2018 |
| JP | 2019-043937 | 3/2019 |
| KR | 10-2011-0047193 | 5/2011 |
| KR | 10-2011-0102198 | 9/2011 |
| WO | WO 2008-054481 | 5/2008 |
| WO | WO 2010/047509 | 4/2010 |
| WO | WO 2011-123495 | 10/2011 |
| WO | WO 2013/173256 | 11/2013 |
| WO | WO 2020/022272 | 1/2020 |

OTHER PUBLICATIONS

Krammer, Novel universal influenza virus vaccine approaches, Current Opinion in Virology, 2016, vol. 17, pp. 95-103.*
Nachbagauer et al., Achimeric haemagglutinin-based influenza split virion vaccine adjuvanted with AS03 induces protective stalk-reactive antibodies in mice, Npj Vaccines, 2016, vol. 1, pp. 1-10.*
[No Author Listed] "The 16th Awaji International Forum on Infection and Immunity Program at a Glance," Poster, Presented at The 16th Awaji International Forum on Infection and Immunity, Japan, Sep. 5-8, 2017, 1 page.
Adachi et al., "Exposure of an occluded hemagglutinin epitope drives selection of a class of cross-protective influenza antibodies," Nature Communications, Aug. 2019, 10(3883):1-13.
Byrd-Leotis et al., "Influenza Hemagglutinin (HA) Stem Region Mutations That Stabilize or Destabilize the Structure of Multiple HA Subtypes," Journal of Virology, Apr. 2015, 89(8):4504-4516.
Doms et al., "Quaternary Structure of Influenza Virus Hemagglutinin after Acid Treatment," Journal of Virology, Dec. 1986, 60(3):833-839.
PCT International Preliminary Report on Patentability in International Appln. No. PCT/JP2018/032537, dated Mar. 10, 2020, 9 pages (with English translation).
PCT International Search Report in International Appln. No. PCT/JP2018/032537, dated Nov. 20, 2018, 6 pages (with English translation).
PCT Written Opinion in International Appln. No. PCT/JP2018/032537, dated Nov. 20, 2018, 7 pages (with English translation).
Takahashi, "Regulation of antibody breadth to mutating viruses through distinct germinal center selection," Poster, Presented at The 16th Awaji International Forum on Infection and Immunity, Japan, Sep. 5-8, 2017, 21 pages.
National Institute of Infectious Diseases, "Minimum Requirements for Biological Products," retrieved from URL <https://www.niid.go.jp/niid/images/qa/seibutuki/MRBP_english/mrbp_2006.pdf>, 2006, 339 pages (English version only).
Sanofi Pasteur, "450 Fluzone Quadrivalent," retrieved from URL <https://www.seacoastmedical.com/storefrontCommerce/forms/ProductInfo/Fluzone%20Quadrivalent%20PI.pdf>, Jun. 2013, 31 pages.

(Continued)

*Primary Examiner* — Benjamin P Blumel
(74) *Attorney, Agent, or Firm* — Fish & Richardson P.C.

(57) ABSTRACT

Provided is a method for producing an influenza HA split vaccine which produces an antibody that binds to a HA stem region of influenza, the HA stem region being less likely to cause antigenic variation, An influenza HA split vaccine is subjected to an acidic treatment. Through the acidic treatment, an influenza HA split vaccine which produces an antibody that binds to a LAH of the HA stem region is obtained. This influenza HA split vaccine has an excellent protective ability against infection of other influenza viruses of different antigenicity.

28 Claims, 7 Drawing Sheets

Specification includes a Sequence Listing.

(56) References Cited

OTHER PUBLICATIONS

EP Extended European Search Report in European Appln. No. 18852584.4, dated Mar. 31, 2021, 7 pages.
Garcia et al., "Dynamic Changes during Acid-Induced Activation of Influenza Hemagglutinin," Structure, Apr. 2015, 23(4):665-676, 13 pages.
Zheng et al., "Influenza H7N9 LAH-HBc virus-like particle vaccine with adjuvant protects mice against homologous and heterologous influenza viruses," Vaccine, Nov. 2016, 34(51):6464-6471.
International Preliminary Report on Patentability in International Appln. No. PCT/JP2020/008974, dated Sep. 16, 2021, 13 pages (with English translation).
International Search Report and Written Opinion in International Appln. No. PCT/JP2020/008974, dated Jun. 9, 2020, 16 pages (with English translation).
Quan et al., "Immunogenicity of low-pH treated whole viral influenza vaccine," Virology, Aug. 2011, 417(1):196-202.
Takahashi, "Abstract: Broadly protective antibodies and vaccines," Presented at U.S.-Japan Cooperative Medical Sciences Program (USJCMSP), 22nd International Conference on Emerging Infectious Diseases in the Pacific Rim, Bangkok, Thailand, Feb. 24, 2020, 10 pages.
Takahashi, "Broadly protective antibodies and vaccines," Presented at U.S.-Japan Cooperative Medical Sciences Program (USJCMSP), 22nd International Conference on Emerging Infectious Diseases in the Pacific Rim, Bangkok, Thailand, Feb. 24, 2020, 23 pages.
Zost et al., "Immunodominance and Antigenic Variation of Influenza Virus Hemagglutinin: Implications for Design of Universal Vaccine Immunogens," The Journal of Infectious Diseases, Apr. 2019, 219(Suppl 1): S38-S45.
U.S. Appl. No. 17/435,590, filed Sep. 1, 2021, Takahashi et al.
Chun et al., "Universal antibodies and their applications to the quantitative determination of virtually all subtypes of the influenza A viral hemagglutinins," Vaccine, Nov. 2008, 26(48):6068-6076.
Extended European Search Report in European Appln. No. 19842246.1, dated Mar. 21, 2022, 12 pages.
Kazaks et al., "Production and purification of chimeric HBc virus-like particles carrying influenza virus LAH domain as vaccine candidates," BMC Biotechnology, Nov. 2017, 17(1), 79, 11 pages.
White et al., "Anti-peptide antibodies detect steps in a protein conformational change: low-pH activation of the influenza virus hemagglutinin," The Journal of Cell Biology, Dec. 1987, 105(6):2887-2896.

Zhou et al., "Improving influenza vaccines: challenges to effective implementation," Current Opinion in Immunology, Apr. 2018, 53:88-95.
Extended European Search Report in European Appln. No. 20766488.9, dated Aug. 25, 2022, 7 pages.
Office Action in U.S. Appl. No. 17/262,021, dated Aug. 4, 2022, 8 pages.
Ren et al., "Epitope-focused vaccine design against influenza A and B viruses," Curr. Opin. Immunol., 2016, 42:83-90.
Goff et al., "Adjuvants and Immunization Strategies to Induce Influenza Virus Hemagglutinin Stalk Antibodies," PLoS One, 2013, 8(11):e79194.
Impagliazzo et al., "A stable trimeric influenza hemagglutinin stem as a broadly protective immunogen," Science, Sep. 18, 2015, 349(6254):1301-1306.
Kostolansky et al., "Inhibition of influenza virus haemolytic and haemagglutination activities by monoclonal antibodies to haemagglutinin glycopolypeptides HA1 and HA2," Acta Virologica, 1989, 33(6):504-512.
Krammer, "The Quest for a Universal Flu Vaccine: Headless HA 2.0," Cell Host Microbe, Oct. 14, 2015, 18(4):395-7.
Nachbagauer et al., "A universal influenza virus vaccine candidate confers protection against pandemic H1N1 infection in preclinical ferret studies," NPJ Vaccines, Sep. 14, 2017, 13 pages.
Office Action in U.S. Appl. No. 17/262,021, dated Dec. 23, 2022, 14 pages.
Steinhagen et al., "TLR-based immune adjuvants," Vaccine, Apr. 2011, 29(17):3341-3355.
Valkenburg et al., "Stalking influenza by vaccination with pre-fusion headless HA mini-stem," Scientific Reports, Apr. 2016, 11 pages.
Yassine et al., "Hemagglutinin-stem nanoparticles generate heterosubtypic influenza protection," Nature Medicine, Aug. 2015, 21(9):1065-1070.
Iwami Kagaku Dictionary, Saburo Nagakura et al. (ed.), Fifth Edition, Nov. 2003, Iwanami Shoten, 327, 3 pages (with partial English translation).
Harrison, "Viral membrane fusion," Nat. Struct. Mol. Biol., Jul. 2008, 15(7):690-698.
Nguyen et al., "Targeting Antigens for Universal Influenza Vaccine Development," Viruses, May 2021, 13(6):973, 21 pages.
Chen et al., "Protection against Multiple Subtypes of Influenza Viruses by Virus-Like Particle Vaccines Based on a Hemagglutinin Conserved Epitope," Biomed Res. Int., Feb. 2015, 2015(901817), 12 pages.

* cited by examiner

SEQUENCE LISTING

```
<160> NUMBER OF SEQ ID NOS: 2

<210> SEQ ID NO 1
<211> LENGTH: 64
<212> TYPE: PRT
<213> ORGANISM: artificial
<220> FEATURE:
<223> OTHER INFORMATION: synthetic H3 polypeptide
<220> FEATURE:
<221> NAME/KEY: MOD_RES
<222> LOCATION: (1)..(1)
<223> OTHER INFORMATION: ACETYLATION

<400> SEQUENCE: 1

Arg Ile Gln Asp Leu Glu Lys Tyr Val Glu Asp Thr Lys Ile Asp Leu
1               5                   10                  15
```

-continued

```
Trp Ser Tyr Asn Ala Glu Leu Leu Val Ala Leu Glu Asn Gln His Thr
            20                  25                  30

Ile Asp Leu Thr Asp Ser Glu Met Asn Lys Leu Phe Glu Lys Thr Arg
        35                  40                  45

Arg Gln Leu Arg Glu Asn Ala Asp Tyr Lys Asp Asp Asp Lys Cys
    50                  55                  60

<210> SEQ ID NO 2
<211> LENGTH: 64
<212> TYPE: PRT
<213> ORGANISM: artificial
<220> FEATURE:
<223> OTHER INFORMATION: synthetic H1 polypeptide
<220> FEATURE:
<221> NAME/KEY: MOD_RES
<222> LOCATION: (1)..(1)
<223> OTHER INFORMATION: ACETYLATION

<400> SEQUENCE: 2

Arg Ile Glu Asn Leu Asn Lys Lys Val Asp Asp Gly Phe Leu Asp Ile
1               5                   10                  15

Trp Thr Tyr Asn Ala Glu Leu Leu Val Leu Leu Glu Asn Glu Arg Thr
            20                  25                  30

Leu Asp Tyr His Asp Ser Asn Val Lys Asn Leu Tyr Glu Lys Val Arg
        35                  40                  45

Ser Gln Leu Lys Asn Asn Ala Asp Tyr Lys Asp Asp Asp Lys Cys
    50                  55                  60
```

METHOD FOR PRODUCING INFLUENZA HA SPLIT VACCINE

This application is a Continuation in Part of International Application No. PCT/JP2018/032537, filed Sep. 3, 2018, which claims priority to JP Application No. 2017-169230, filed Sep. 4, 2017 and JP Application No. 2018-137952, filed Jul. 23, 2018, the disclosures of which are incorporated herein by reference.

TECHNICAL FIELD

The present invention relates to a method for producing an influenza HA split vaccine.

The instant application includes a sequence listing in electronic medium and submitted to the United States Patent and Trademark Office via the electronic filing system. The ASCII text file, which is incorporated-by-reference herein, is titled "48110-0002001_ST25.txt," was created on Dec. 16, 2020, and has a size of 2 kilobytes.

BACKGROUND ART

Current influenza haemagglutinin (hereinafter also abbreviated as "HA") vaccines induce an anti-HA antibody, thereby exerting a protective effect against infection. The anti-HA antibody binds to a portion of a virus called a "head region" externally exposed from a virus membrane. This region most frequently undergoes structural change in a viral strain. Therefore, in some cases, the anti-HA antibody may fail to bind to a virus which causes antigenic variation and is different from the vaccine strain, and the vaccine cannot exert the protective effect against the infection.

Recently, it has been revealed that antibodies that bind to a stem region which is less likely to cause antigenic variation include protective antibodies against infection (Patent Document 1). In order to efficiently induce the antibody that binds to the stem region, a HA stem protein having a stabilized stem portion has been developed, and its clinical trial in humans has been carried out: the stem portion, which is originally unstable, has been stabilized through artificial variation or binding of linkers.

However, problems about the production for practical use still remain to be solved, and development of a HA vaccine antigen that can induce an anti-stem antibody more easily has been expected.

CITATION LIST

Patent Document

Patent Document 1: Japanese Unexamined Patent Publication (Translation of PCT International Application) No. 2016-516090

SUMMARY OF THE INVENTION

Technical Problem

In view of the foregoing, it is an object of the present invention to provide a method for producing an influenza HA split vaccine which produces an antibody that binds to a HA stem region, which is less likely to cause antigenic variation, of influenza.

Solution to the Problem

The method for producing a HA split vaccine according to the present invention includes subjecting an influenza HA split vaccine to an acidic treatment, thereby producing an influenza HA split vaccine which produces an antibody that binds to a long alpha helix (LAH) of a HA stem region, and is effective against an influenza virus that causes antigenic variation.

Specifically, the present invention relates to the following.

[Item 1] A method for producing an influenza HA split vaccine which produces an antibody that binds to a LAH of a HA stem region, the method including: subjecting an influenza HA split vaccine to an acidic treatment.

[Item 1a] A method for producing an influenza HA split vaccine which produces an antibody that binds to a LAH of a HA stem region, the method including: subjecting an influenza HA split vaccine, which has not undergone a formalin treatment, to an acidic treatment.

[Item 1b] A method for producing an influenza HA split vaccine which produces an antibody that binds to a LAH of a HA stem region, the method including: subjecting an influenza HA split vaccine to an acidic treatment, and thereafter, subjecting the influenza HA split vaccine to a formalin treatment.

[Item 1c] A method for producing an influenza HA split vaccine which produces an antibody that binds to a LAH of a HA stem region, the method including: subjecting an influenza HA split vaccine, which has not undergone a formalin treatment, to an acidic treatment, and thereafter, subjecting the influenza HA split vaccine to a formalin treatment.

[Item 2] The production method according to Items 1 and 1a to 1c, wherein the influenza HA split vaccine is also effective against an influenza virus that causes antigenic variation.

[Item 3] A method for producing an influenza HA split vaccine which produces an antibody that binds to a LAH of a HA stem region and which is effective against an influenza virus that causes antigenic variation, the method including: subjecting an influenza HA split vaccine to an acidic treatment.

[Item 4] The method of any one of Items 1 to 3 and 1a to 1c, wherein the acidic treatment is performed at a pH of 4.4 to 5.8.

[Item 5] The method of any one of Items 1 to 4 and 1a to 1c, wherein the influenza HA split vaccine is of type H3N2 or type H1N1.

[Item 5a] The method for producing an influenza HA split vaccine according to any one of Items 1 to 5 and 1a to 1c, wherein the influenza HA split vaccine is an influenza HA split vaccine of a single HA subtype.

[Item 5b] The method for producing an influenza HA split vaccine according to any one of Items 1 to 5 and 1a to 1c, the method including: mixing two or more of influenza HA split vaccine antigens, each of which is produced by subjecting an influenza HA split vaccine of a single subtype to an acidic treatment.

[Item 6] An influenza HA split vaccine which produces an antibody that binds to a LAH of a HA stem region.

[Item 7] The influenza HA split vaccine of Item 6, which is also effective against an influenza virus that causes antigenic variation.

[Item 8] The influenza HA split vaccine of Item 6 or 7, which has a HA stem region exposed outside.

[Item 9] The influenza HA split vaccine of any one of Items 6 to 8, wherein the HA stem region of the influenza HA split vaccine antigen, which is exposed outside, enhances the antigenicity of the LAH of the HA stem region, and the influenza HA split vaccine is capable of producing an antibody that binds to the LAH of the HA stem region.

[Item 10] An influenza HA split vaccine which is effective against an influenza virus that causes antigenic variation, and which produces an antibody that binds to a LAH of a HA stem region, the vaccine being produced by subjecting an influenza HA split vaccine to an acidic treatment.

[Item 10a] An influenza HA split vaccine produced by subjecting an influenza HA split vaccine, which has not undergone a formalin treatment, to an acidic treatment, the influenza HA split vaccine producing an antibody that binds to a LAH of a HA stem region.

[Item 10b] An influenza HA split vaccine produced by a production process including: subjecting an influenza HA split vaccine to an acidic treatment; and thereafter, subjecting the influenza HA split vaccine to a formalin treatment, the influenza HA split vaccine producing an antibody that binds to a LAH of a HA stem region.

[Item 10c] An influenza HA split vaccine produced by a production process including: subjecting an influenza HA split vaccine, which has not undergone a formalin treatment, to an acidic treatment; and thereafter, subjecting the influenza HA split vaccine to a formalin treatment, the influenza HA split vaccine producing an antibody that binds to a LAH of a HA stem region.

[Item 10d] An influenza HA split vaccine produced by subjecting an influenza HA split vaccine including a single subtype to an acidic treatment, the influenza HA split vaccine producing an antibody that binds to a LAH of a HA stem region.

[Item 10e] An influenza HA split vaccine which is a vaccine antigen produced by mixing two or more of influenza HA split vaccine antigens each of which is produced by subjecting an influenza HA split vaccine including a single subtype to an acidic treatment, the influenza HA split vaccine producing an antibody that binds to a LAH of a HA stem region.

[Item 10f] An influenza HA split vaccine of any one of Items 10 to 10e, which is also effective against an influenza virus that causes antigenic variation.

[Item 11] An influenza HA split vaccine which is produced by subjecting an influenza HA split vaccine to an acidic treatment, produces an antibody that binds to a LAH of a HA stem region, and is also effective against an influenza virus that causes antigenic variation.

Advantages of the Invention

According to the present invention, an influenza HA split vaccine which produces an antibody that binds to a HA stem region of influenza is obtained by a simple technique, the HA stem region being less likely to cause antigenic variation. Therefore, an influenza HA split vaccine which is also effective against an influenza virus which causes antigenic variation is obtained.

DESCRIPTION OF EMBODIMENTS

Embodiments of the present invention will be described in detail below with reference to the accompanying drawings. However, the embodiments are intended to facilitate understanding of the principle of the present invention, and the scope of the invention is not limited to the following embodiments. Other embodiments, in which the configuration of the following embodiments has been appropriately replaced by those skilled in the art, are also encompassed in the scope of the present invention.

The method for producing an influenza HA split vaccine according to this embodiment includes a step of subjecting an influenza HA split vaccine to an acidic treatment.

An influenza HA split vaccine is prepared through a treatment of a whole-virus vaccine with ether to remove lipid components which become pyrogens. The influenza HA split vaccine has HA protein as the main ingredient because the influenza HA split vaccine is produced by collecting the HA protein, which is required for immunization, from the surfaces of the virus particles by density gradient centrifugation.

Figure 1:
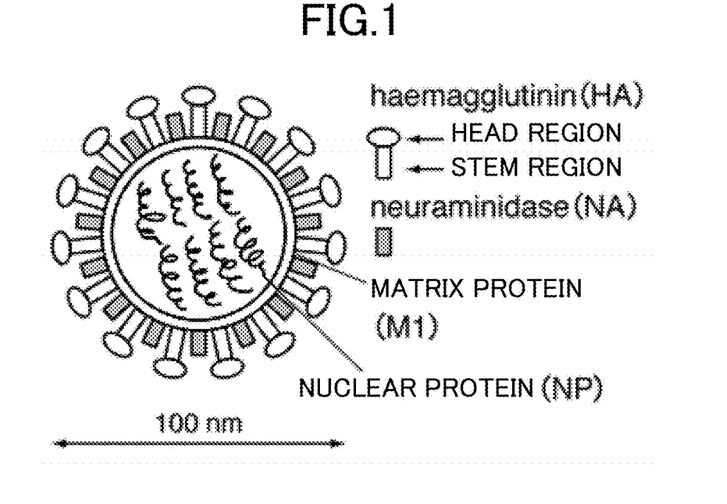
FIG. 1 is a schematic diagram illustrating an influenza virus.

Glycoprotein called "spike protein" protrudes from the surface of an influenza virus (FIG. 1). An influenza A virus has two types of spike proteins, namely, HA and NA (neuraminidase), which help the virus cause the infection. HA binds to a cell to be infected and helps the entry of the virus into the cell. HA frequently causes antigenic variation. NA unbinds the infected cell from HA, and serves to release the replicated viruses from the cell.

HA of the influenza A virus is divided into two regions, namely, a head region and a stem region (FIG. 1). The head region contains a receptor binding site at which the virus binds to a target cell. The stem region contains a fusion peptide sequence necessary for membrane fusion between the viral membrane and the cell membrane of the target cell.

An acidic treatment on the influenza HA split vaccine changes the structure of the HA protein to a structure called membrane fusion-type. In the membrane fusion-type HA protein, the stem region is exposed outside from the viral membrane instead of the head region, with a large structural change in the conformation of an antigen stem. The present inventors have found in vivo that when the membrane fusion-type HA protein is used as a vaccine, an antibody that binds to a LAH of the stem region is induced, and that this antibody has a protective effect against a virus strain that causes antigenic variation. The present invention has been made based on this fact.

The acidic treatment is not particularly limited, and may be performed at a pH of, for example, 3.0 to 6.5, preferably 4.0 to 6.0, and more preferably 4.4 to 5.8. The acid for use in the acidic treatment is not particularly limited, and may be, for example, phosphoric acid, citric acid, maleic acid, or any other suitable acid.

Based on differences in antigenicity, HA of the influenza A virus is classified into 18 subtypes (H1 to H18), and NA into 9 subtypes (N1 to N9). The influenza HA split vaccine of the present invention is applicable to all of these subtypes. In addition, the method for producing the influenza HA split vaccine according to the present invention can produce a vaccine which is effective against not only the influenza A virus, but also an influenza B virus having HA.

The influenza split HA vaccine obtained by the production method according to the present invention produces an antibody that binds to a LAH which is less likely to cause variation. Therefore, the vaccine can be cross-protective against an influenza virus, which is known as an antigenic variant, as long as the virus has the same HA subtype. Furthermore, the influenza split HA vaccine obtained by the production method according to the present invention may be cross-reactive between HA subtypes of similar amino acid sequences of LAH (e.g., H3 and H7).

In the present application, an "influenza HA split vaccine of a single HA subtype" refers to an influenza HA split vaccine of a single HA subtype which is selected from the 18 subtypes (H1 to H18) of the influenza A virus, or the influenza B virus. As long as with the single HA subtype, the NA subtypes may be identical or different. Preferred HA subtypes include H1, H3, and B.

To produce a mixed vaccine containing two or more HA subtypes, influenza HA split vaccines each of which is of a single HA subtype are subjected to an acidic treatment, and a plurality of (two or more) influenza HA split vaccines thus obtained can be mixed together. Alternatively, a mixed vaccine can also be produced by performing an acidic treatment on an influenza HA split vaccine previously prepared by mixing vaccines of two or more HA subtypes. To inoculate the vaccine as a vaccine including two or more subtypes, the vaccine preferably includes one to three subtypes selected from the group consisting of H1, H3, and B.

In a preferred embodiment, the influenza HA split vaccine obtained by the production method of the present invention binds to a LAH binding monoclonal antibody more strongly than a current HA split vaccine. For example, the influenza HA split vaccine binds to the LAH binding monoclonal antibody at least 1.05 times, preferably at least 1.1 times, more preferably at least 1.5 times, and even more preferably at least two times more strongly than the current HA split vaccine. In this context, "the influenza HA split vaccine binds at least 1.05 times, at least 1.1 times, at least 1.5 times, or at least two times more strongly than the current HA split vaccine" means, for example, that the reciprocal of the antibody concentration at the time when an absorbance determined by regression is 0.7 is at least 1.05 times, at least 1.1 times, at least 1.5 times, or at least two times the reciprocal of the antibody concentration of the current HA split vaccine. In a preferred embodiment, the binding capacity of the influenza HA split vaccine of the present invention to the LAH binding monoclonal antibody is higher than that of the current HA split vaccine. Although the upper limit is not particularly limited, the binding capacity may be in a range of, for example, 1.05 to 200 times, 1.1 to 150 times, 1.5 to 100 times, or 2 to 50 times. Alternatively, the range of the binding capacity of the influenza HA split vaccine of the present invention to the LAH binding monoclonal antibody compared to that of the current HA split vaccine may be indicated by a combination of the lower limit value selected from 1.05, 1.1, 1.5, 2, 3, 4, and 5 and the upper limit value selected from 200, 150, 100, 50, 30, and 20. For the measurement of the binding capacity of the influenza HA split vaccine to the LAH binding monoclonal antibody, any method can be used without particular limitations, and a common method known to those skilled in the art can be employed. For example, the binding capacity can be measured by a method described in examples of the present application.

In the present application, the "LAH binding monoclonal antibody" means a monoclonal antibody which binds to the LAH. For the production of the monoclonal antibody, any method may be used without particular limitations, and a common method known to those skilled in the art may be employed. In the measurement of the binding capacity of the influenza HA split vaccine to the LAH binding monoclonal antibody, it is assumed that the LAH binding monoclonal antibody is capable of binding to a peptide corresponding to at least a portion of the LAH of an influenza virus from which the influenza HA split vaccine is derived.

In this application, the "current HA split vaccine" means a vaccine from which lipid components that become pyrogens are removed through a treatment of the whole-virus vaccine with ether, and can be produced by a method described in Example 1 of the present application, for example. The current HA split vaccine may also be an influenza HA split vaccine produced without being subjected to an acidic treatment, in contrast with the influenza HA split vaccine of the present invention prepared by a method including the following acidic treatment.

The production of the influenza HA split vaccine of the present invention may include performing a formalin treatment. In a preferred embodiment, the acidic treatment of the influenza HA split vaccine is performed before the formalin treatment. In preparing an influenza HA split vaccine antigen of the present invention (an influenza HA split vaccine antigen capable of producing an antibody that binds to the LAH of the HA stem region), a HA fraction for use for the current influenza HA split vaccine is subjected to an acidic treatment, and then to a formalin treatment. This makes it possible to obtain an influenza HA split vaccine antigen which produces a cross-reactive antibody more effectively, and thus, is more preferable as a universal influenza vaccine antigen. That is, in a preferred embodiment of the present application, a HA fraction from which fat solvents are removed through a treatment of the virus particles with ether or any other appropriate agents is subjected to an acidic treatment, and then to a formalin treatment.

In a preferred embodiment of the present application, the influenza HA split vaccine before the acidic treatment is a split vaccine which has not undergone the formalin treatment. Commercially available Influenza HA Vaccine (trade name) has already undergone a treatment with formaldehyde or a substance having an equivalent action after the virus is decomposed by ether or any other appropriate agents and fat solvents are removed, as described in Biological Products Standards (Mar. 30, 2004, Ministerial Notification No. 155 of Ministry of Health, Labor and Welfare, most recent revision on Nov. 30, 2018, Ministerial Notification No. 409). It is preferable not to use the commercially available Influenza HA Vaccine (trade name), which is one of the influenza HA split vaccines, for the production of the influenza HA split vaccine of the present invention because it has already been treated with formaldehyde or any other appropriate agents.

The concentration of formalin in a formalin treatment solution for used in the formalin treatment of the influenza HA split vaccine after the acidic treatment is, for example, 0.0005 v/v % to 10 v/v %, preferably 0.001 v/v % to 1 v/v %, more preferably 0.003 v/v % to 0.5 v/v %, and still more preferably 0.005 v/v % to 0.1 v/v %. It is preferable to use formalin of a medical grade.

The method for producing the influenza HA split vaccine of the present invention may include a step of adding an adjuvant. Examples of the adjuvant include, but are not limited to, aluminum salts such as aluminum hydroxide and aluminum phosphate, chitosan, oligodeoxynucleotides, and oil-in-water emulsions. Among them, aluminum hydroxide is preferred, and use of aluminum hydroxide as the adjuvant can enhance the immunogenicity.

The influenza HA split vaccine obtained by the production method of the present invention can be used, for example, for additional inoculation after a predetermined period after the initial inoculation. The period after the initial inoculation and before the additional inoculation is not particularly limited, but may be, for example, twenty days to three years, preferably three months to two years, more preferably six months to one year. The amount of the influenza HA split vaccine for the initial and additional inoculations is not particularly limited, but may be, for example, 1 μg to 200 μg, preferably 10 μg to 30 μg, more preferably 15 μg, per dose. A single dose is, for example, 0.5 mL. Any administration method may be used for the initial and additional inoculations without particular limitations, and for example, nasal, subcutaneous, intradermal, transdermal, intraocular, mucosal, or oral administration may be employed. Intramuscular administration is preferred.

The influenza HA split vaccine obtained by the production method of the present invention has a protective effect against a virus strain that causes antigenic variation. For example, if a current HA split vaccine is prepared from particles of H3N2 influenza virus (A/Fujian/411/02 (H3N2)) and subjected to an acidic treatment, the vaccine can have a protective effect against infection of not only A/Fujian/411/02 (H3N2), but also A/Guizhou/54/89 (H3N2), A/OMS/5389/88 (H3N2), A/Beijing/32/92 (H3N2), A/England/427/88 (H3N2), A/Johannesburg/33/94 (H3N2), A/Leningrad/360/86 (H3N2), A/Mississippi/1/85 (H3N2), A/Philippines/2/82 (H3N2), A/Shangdong/9/93 (H3N2), A/Shanghai/16/89 (H3N2), A/Shanghai/24/90 (H3N2), A/Sichuan/2/87 (H3N2), A/Kitakyushyu/159/93 (H3N2), A/Akita/1/94 (H3N2), A/Panama/2007/99 (H3N2), A/Wyoming/03/03 (H3N2), A/New York/55/2004 (H3N2), or A/Hiroshima/52/2005 (H3N2), for example. Also, for example, if a current HA split vaccine is prepared from particles of H1N1 influenza virus (A/Puerto Rico/8/34 (H1N1)) and subjected to an acid treatment, the vaccine can also have a protective effect against infection of not only A/Puerto Rico/8/34 (H1N1), but also A/Narita/1/09 (H1N1), A/Beijing/262/95 (H1N1), A/Brazil/11/78 (H1N1), A/Chile/1/83 (H1N1), A/New Jersey/8/76 (H1N1), A/Taiwan/1/86 (H1N1), A/Yamagata/32/89 (H1N1), A/New Caledonia/20/99 (H1N1), A/Solomon Islands/3/2006 (H1N1), A/Brisbane/59/2007 (H1N1), or A/Mexico/4108/2009 (H1N1), for example.

EXAMPLES

1. Preparation of HA Split Vaccine

Tween 80 was added to particles of H3N2 influenza virus (strain X31) or particles of H1N1 influenza virus (A/Puerto Rico/8/34 strain) suspended in phosphate buffered saline to a final concentration of 0.1 v/v %, and suspended therein. Diethyl ether was added and suspended, and the suspension was left stand until an aqueous layer and a diethyl ether layer were completely separated, and then the diethyl ether layer was removed. After repeating this ether extraction, diethyl ether remaining in the recovered aqueous layer was distilled off at normal pressure to obtain an HA split vaccine.

2. Acidic Treatment

The HA split vaccine was suspended in phosphate buffered saline, and an acidic treatment was then performed by adding 0.15 M citrate buffer (pH 3.5) to bring the pH to 5.0. After standing at room temperature for 30 minutes, 1 M Tris buffer (pH 8.0) was added so that the pH was returned to 7.3. Thereafter, centrifugation was performed to obtain a membrane fusion-type HA split vaccine. Formalin was added to the membrane fusion-type HA split vaccine thus prepared to a final concentration of 0.05 v/v %, and left stand for several days.

A current HA split vaccine was prepared in the same manner as described in 1 above except that no acidic treatment was provided.

3. Measurement of Titer of Anti-LAH Antibody by ELISA 3-1. Inoculation of H3N2 Influenza Vaccine BALB/c mice (female, 6 to 12 weeks old) were intraperitoneally inoculated with the current H3N2 HA split vaccine or the membrane fusion-type HA split vaccine (10 μg of vaccine+10 v/v % of AddaVax adjuvant (InvivoGen) dissolved in phosphate buffered saline to a liquid volume of 200 μl). Twenty eight days after the initial inoculation, the mice were intraperitoneally inoculated with the membrane fusion-type HA vaccine (10 μg of the vaccine alone was dissolved in phosphate buffered saline to a liquid volume of 200 μl). At least 14 days after the additional inoculation, blood was collected from the mice inoculated with the vaccine, from which sera were collected.

3-2. Measurement by ELISA

The concentration of the anti-LAH antibody in the sera of BALB/c mice intraperitoneally inoculated with the current H3N2 HA split vaccine or the membrane fusion-type HA split vaccine was measured by ELISA (Enzyme-Linked Immuno Sorbent Assay) in the following manner.

Specifically, a synthetic peptide (H3; Ac-RIQDLEKYVEDTKIDLWSYNAELLVA-LENQHTIDLTDSEMNKLFEKTRRQLRENADY KDDDDKC) (SEQ ID NO: 1) corresponding to a portion (long alpha helix) of the stem portion was dissolved in phosphate buffered saline (pH 7.3) at 10 μg/ml, and added to 96-well plates by 100 μl each. After standing overnight at 4° C., each well was washed three times with phosphate buffered saline, and 150 μl of phosphate buffered saline containing 1 v/v % bovine serum albumin was added. After standing at room temperature for two hours, each well was washed three times with phosphate buffered saline. Then, 100 μl of a mouse serum serially diluted with phosphate buffer containing 0.05 v/v % of Tween 20 and 1 v/v % bovine serum albumin, and 100 μl of a standard monoclonal antibody of known concentration (H3; clone name V15-5) were added to each well. After standing at room temperature for two hours, each well was washed three times with phosphate buffered saline (containing 0.05 v/v % of Tween 20), and 100 μl of a peroxidase-labeled anti-mouse IgG antibody (Southern Biotech) diluted with phosphate buffered saline containing 0.05 v/v % Tween 20 and 1 v/v % bovine serum albumin was added to each well. After standing at room temperature for two hours, each well was washed three times with phosphate buffered saline (containing 0.05 v/v % of Tween 20). Then, 30 mg of o-phenylendiamine tablet (Sigma) and 24 µl of 30% hydrogen peroxide solution (30% w/w; Sigma) were added to 60 ml of citrate buffer (pH 5.0) as a substrate, and 100 µl of the resultant was added to each well. After the color development, 50 µl of 1 mol/L sulfuric acid (Wako Pure Chemical Industries, Ltd.) was added to stop the reaction, and an absorbance value at 490 nm was measured using a Microplate Reader 450 (Biorad).

Figure 2:
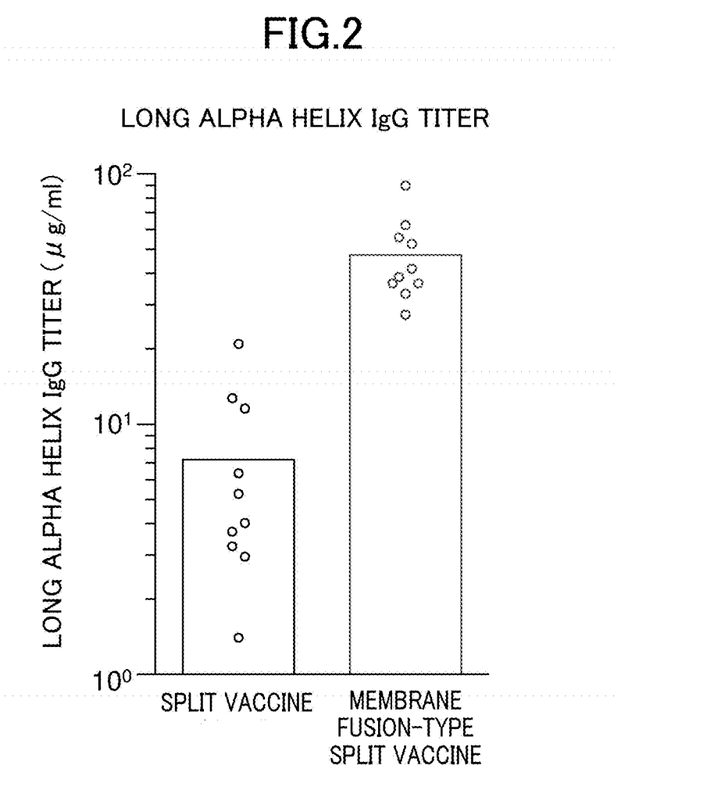
FIG. 2 is a graph showing an increase in the titer of an anti-LAH antibody in sera of mice inoculated with a membrane fusion-type H3N2 HA split vaccine.

As shown in FIG. 2, the titer of the anti-LAH antibody in the serum of the BALB/c mice intraperitoneally inoculated with the membrane fusion-type HA split vaccine was significantly higher than the titer of the anti-LAH antibody in the serum of BALB/c mice intraperitoneally inoculated with the current HA split vaccine.

4. Cross-Protection Against Antigenic Variant

In an experiment on protection against infection with the H3N2 virus, 200 µl of a serum collected from uninoculated mice, 200 µl of a serum collected from mice inoculated with the current H3N2 HA split vaccine, or 200 µl of a serum collected from mice inoculated with the membrane fusion-type HA split vaccine was intraperitoneally administered to BALB/c mice (female, 6 to 12 weeks old).

Three hours after the serum administration, another H3N2 influenza virus (A/Guizhou/54/89) having different antigenicity from the vaccine strain was intranasally administered at 5 mouse lethal dose 50 (five times the amount of virus lethal to 50% of mice) under anesthesia.

Mice were weighed and observed daily for 21 days from the viral infection to study the change in body weight and the survival rate. Mice that lost 25% of their weight were sacrificed.

Figure 3:
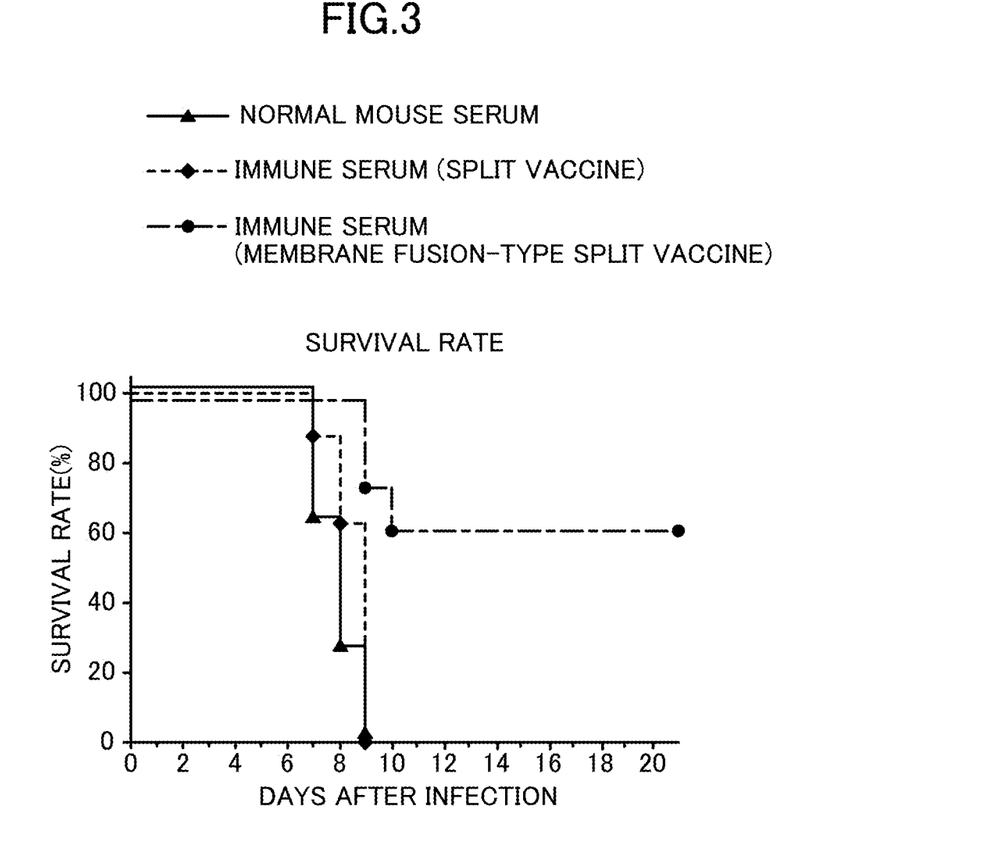
FIG. 3 is a graph showing an improvement in the cross-protective capacity of mice inoculated with the membrane fusion-type H3N2 HA split vaccine against an antigenic variant.

As shown in FIG. 3, regarding the BALB/c mice inoculated with the membrane fusion-type HA split vaccine, the decrease in the survival rate was significantly curbed on and after the ninth day after the infection with the other H3N2 influenza virus of different antigenicity.

5. Measurement of Titer of Anti-LAH Antibody by ELISA 5-1. Particles of H1N1 Influenza Virus C57BL/6 mice (female, 6 to 12 weeks old) were intraperitoneally inoculated with a current H1N1 HA split vaccine or a membrane fusion-type HA split vaccine (10 µg of vaccine+10 µg of CpG-ODN 1760 suspended in phosphate buffered saline and mixed with an equal volume of Freund's incomplete adjuvant (ROCKLAND) to a liquid volume of 200 µl). Twenty eight days after the initial inoculation, the mice were intraperitoneally inoculated with the membrane fusion-type HA split vaccine (10 µg of vaccine+10 µg of CpG-ODN suspended in phosphate buffered saline and mixed with an equal volume of Freund's incomplete adjuvant (ROCKLAND) to a liquid volume of 200 µl, in the same manner as the initial inoculation). At least 14 days after the additional inoculation, blood was collected from the mice inoculated with the vaccine, from which sera were collected.

5-2. Measurement by ELISA

The concentration of the anti-LAH antibody in the sera of C57BL/6 mice intraperitoneally inoculated with the current H1N1 HA split vaccine or the membrane fusion-type HA split vaccine was measured by ELISA in the following manner.

The measurement was performed in the same manner as described above except that a synthetic peptide (H1; Ac-RIENLNKKVDDGFLDIWTYNAELLVLLEN-ERTLDYHDSNVKNLYEKVRSQLKNNAD YKDDDDKC) (SEQ ID NO: 2) corresponding to a portion (long alpha helix) of the stem portion was used and a standard monoclonal antibody of known concentration (H1; clone name F2) was used.

Figure 4:
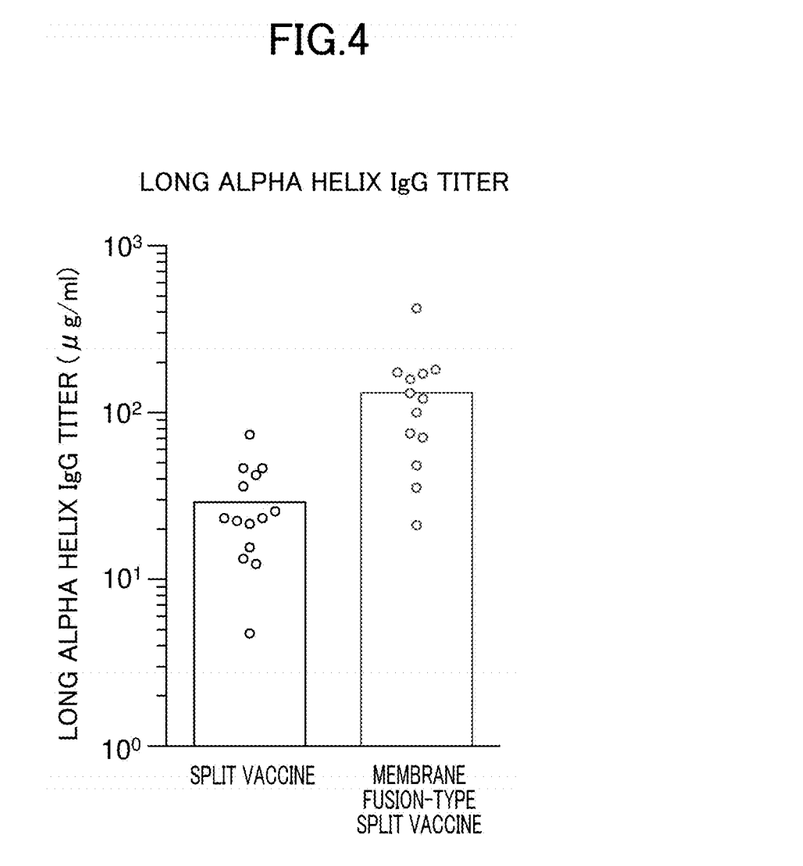
FIG. 4 is a graph showing an increase in the titer of an anti-LAH antibody in sera of mice inoculated with a membrane fusion-type H1N1 HA split vaccine.

As shown in FIG. 4, the titer of the anti-LAH antibody in the sera of the C57BL/6 mice intraperitoneally inoculated with the membrane fusion-type HA split vaccine was significantly higher than the titer of the anti-LAH antibody in the sera of the C57BL/6 mice intraperitoneally inoculated with the current HA split vaccine.

6. Cross-Protection Against Antigenic Variant

In an experiment on protection against infection with the H1N1 virus, 200 µl of a serum collected from uninoculated mice, 200 µl of a serum collected from mice inoculated with the current H1N1 HA split vaccine, or 200 µl of a serum collected from mice inoculated with the membrane fusion-type HA split vaccine was intraperitoneally administered to C57BL/6 mice (female, 6 to 12 weeks old).

Three hours after the serum administration, another H1N1 influenza virus (A/Narita/1/09) having different antigenicity from the vaccine strain was intranasally administered at 5 mouse lethal dose 50 (five times the amount of virus lethal to 50% of mice) under anesthesia.

Figure 5:
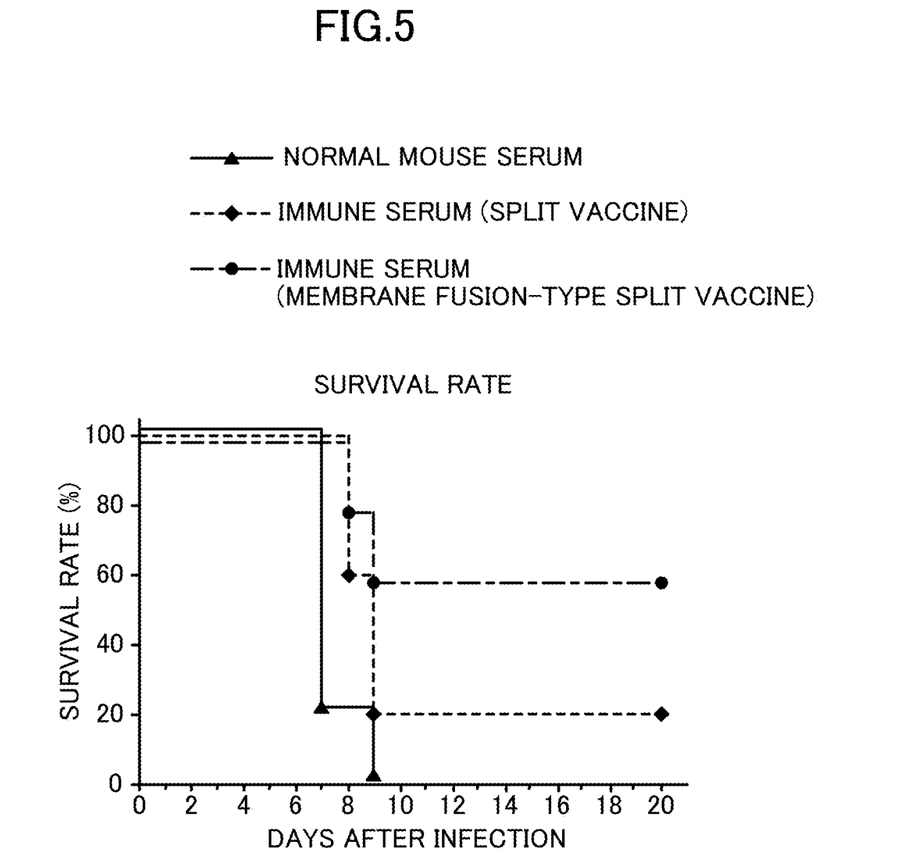
FIG. 5 is a graph showing an improvement in the cross-protective capacity of mice inoculated with the membrane fusion-type H1N1 HA split vaccine against an antigenic variant.

Mice were observed daily for 20 days from the viral infection to study the survival rate. As shown in FIG. 5, regarding the C57BL/6 mice inoculated with the membrane fusion-type HA split vaccine, the decrease in the survival rate was significantly curbed on and after the ninth day after the infection with the other H1N1 influenza virus of different antigenicity.

7. Binding Capacity of Antibody to LAH Epitope

Binding of anti-LAH monoclonal antibodies (#1 to #5 in FIG. 6) prepared from murine or human peripheral blood infected with strain X31 to a current HA split vaccine or a membrane fusion-type HA split vaccine was measured by ELISA (Enzyme-Linked Immuno Sorbent Assay). The current HA split vaccine or membrane fusion-type HA split vaccine of an H3N2 influenza virus (strain X31) was dissolved in phosphate buffered saline (pH 7.3), and added to a 96-well plate by 50 µl each. After standing overnight at 4° C., each well was washed three times with phosphate buffered saline, and 150 µl of phosphate buffered saline containing 1 v/v % bovine serum albumin was added. After standing at room temperature for two hours, each well was washed three times with phosphate buffered saline (containing 0.05 v/v % of Tween 20), and 50 µl of the LAH binding monoclonal antibody serially diluted with phosphate buffer containing 1 v/v % bovine serum albumin was added. After standing overnight at 4° C., each well was washed three times with phosphate buffered saline (containing 0.05 v/v % of Tween 20), and 100 µl of a peroxidase-labeled anti-mouse IgG antibody (Southern Biotech) diluted with phosphate buffered saline containing 0.05 v/v % Tween 20 and 1 v/v % bovine serum albumin was added to each well. After standing at room temperature for two hours, each well was washed three times with phosphate buffered saline (containing 0.05 v/v % of Tween 20). Then, 30 mg of o-phenylendiamine tablet (Sigma) and 24 µl of 30% hydrogen peroxide solution (30% w/w; Sigma) were added to 60 ml of citrate buffer (pH 5.0) as a substrate, and 50 µl of the resultant was added to each well. After the color development, 25 µL of 1 mol/L sulfuric acid (Wako Pure Chemical Industries, Ltd.) was added to stop the reaction, and an absorbance value at 490 nm was measured using Microplate Reader 450 (Biorad). The change in binding capacity was calculated from the absorbance values measured with respect to the current HA split vaccine or the membrane fusion-type HA split vaccine.

Figure 6:
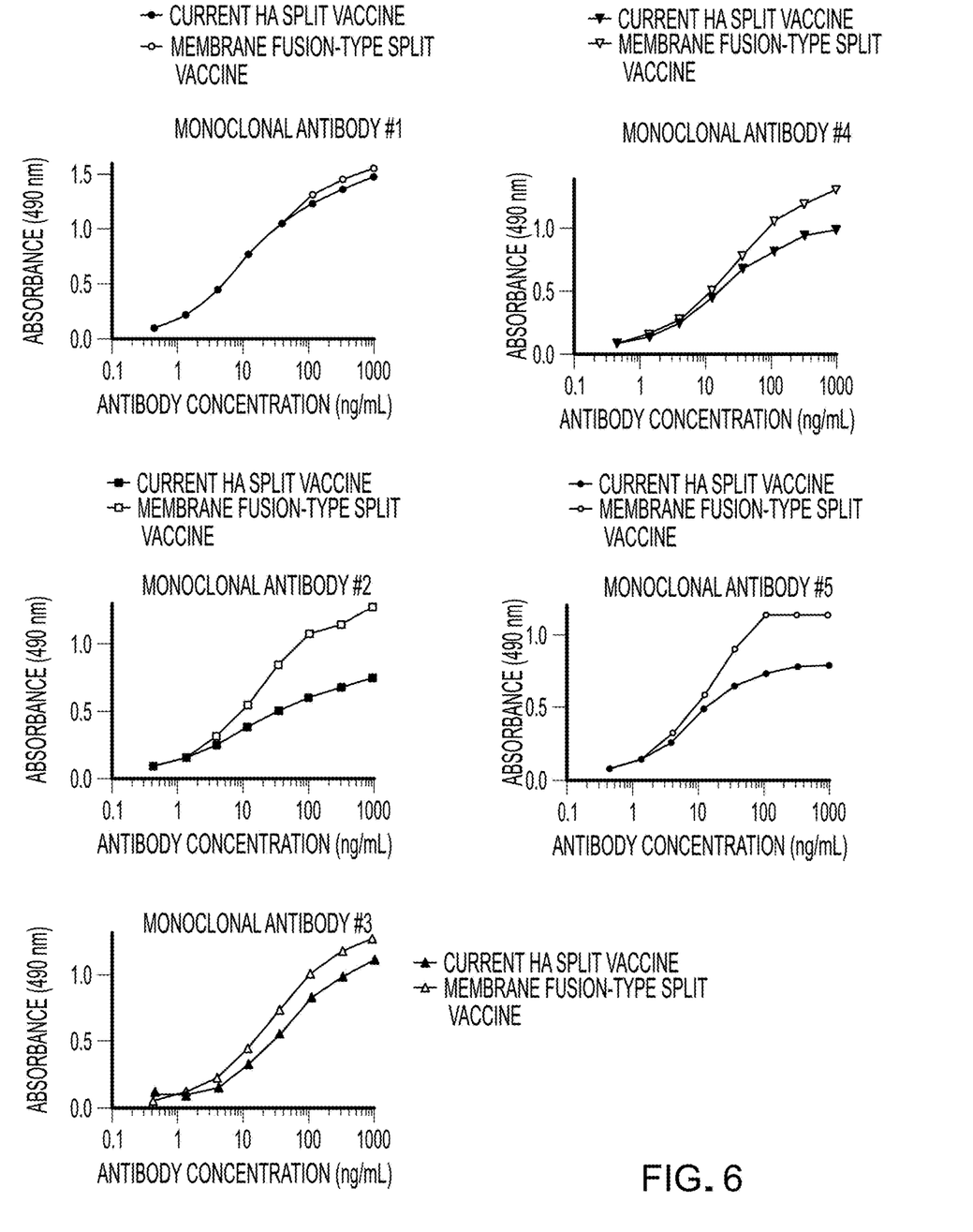
FIG. 6 shows graphs each indicating that a LAH binding monoclonal antibody binds more strongly to a membrane fusion-type HA split vaccine than to a current HA split vaccine.

As shown in FIG. 6, the binding capacity of the LAH binding monoclonal antibody to the membrane fusion-type HA split vaccine was 1.05 to 21 times greater than the binding capacity to the current HA split vaccine. The results show that an acidic treatment of the HA split vaccine enhances the binding capacity of the antibody to the LAH epitope.

8. Influence of Order of Formalin Treatment on Binding Capacity of Antibody and Antibody Inducibility 8-1. Preparation of Formalin-Pretreated HA Split Vaccine To particles of H3N2 influenza virus (strain X31) suspended in phosphate buffered saline, Tween 80 was added and suspended in a final concentration of 0.1 v/v %. Diethyl ether was added and suspended, and the suspension was left stand until an aqueous layer and a diethyl ether layer were completely separated, and then the diethyl ether layer was removed. After repeating this ether extraction, diethyl ether remaining in the recovered aqueous layer was distilled off at normal pressure. Further, formalin was added at a final concentration of 0.05 v/v %, and the mixture was left stand for several days to obtain a formalin-pretreated HA split vaccine.

8-2. Acidic Treatment of Formalin-Pretreated HA Split Vaccine

The formalin-pretreated HA split vaccine was suspended in phosphate buffered saline, and then an acidic treatment was performed by adding 0.15 M citrate buffer (pH 3.5) to bring the pH to 5.0. After standing at room temperature for 30 minutes, 1 M Tris buffer (pH 8.0) was added so that the pH was returned to 7.3. Thereafter, centrifugation was performed.

9. Binding Capacity of Antibody to LAH Epitope

The binding capacity of the antibody to the LAH epitope was measured in the same manner as described in 7 above, and the change in the binding capacity was calculated. Here, the same antibodies as #2, #4 and #5 shown in FIG. 6 were used as the monoclonal antibodies, and the monoclonal antibody #6 which binds to the HA head region was used as a control.

10. Measurement of Titer of Anti-LAH Antibody by ELISA 10-1. Inoculation of H3N2 Influenza Vaccine BALB/c mice (female, 6 to 12 weeks old) were intraperitoneally inoculated with the current H3N2 HA split vaccine or the membrane fusion-type HA split vaccine (10 μg vaccine+10 v/v % AddaVax adjuvant (InvivoGen) dissolved in phosphate buffered saline to a liquid volume of 200 μl). At least 12 days after the inoculation, blood was collected from the mice inoculated with the vaccines, from which sera were collected.

10-2. Measurement by ELISA

The titer of the anti-LAH antibody was measured in the same manner as described in 3-2 above.

Figure 7:
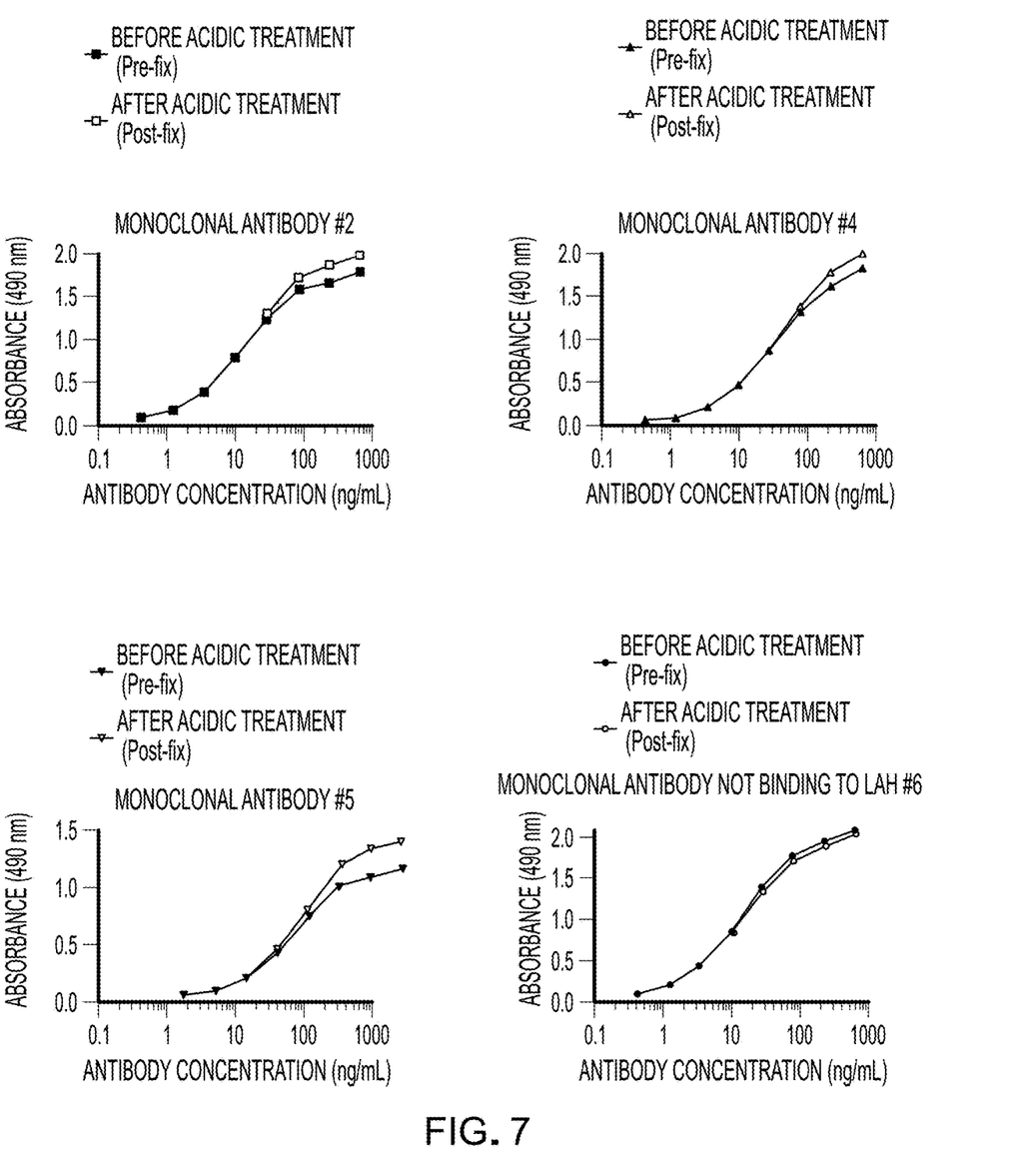
FIG. 7 shows graphs each indicating that the LAH binding monoclonal antibody strongly binds to a membrane fusion-type HA split vaccine that has been subjected to a formalin treatment after an acidic treatment.
Figure 8:
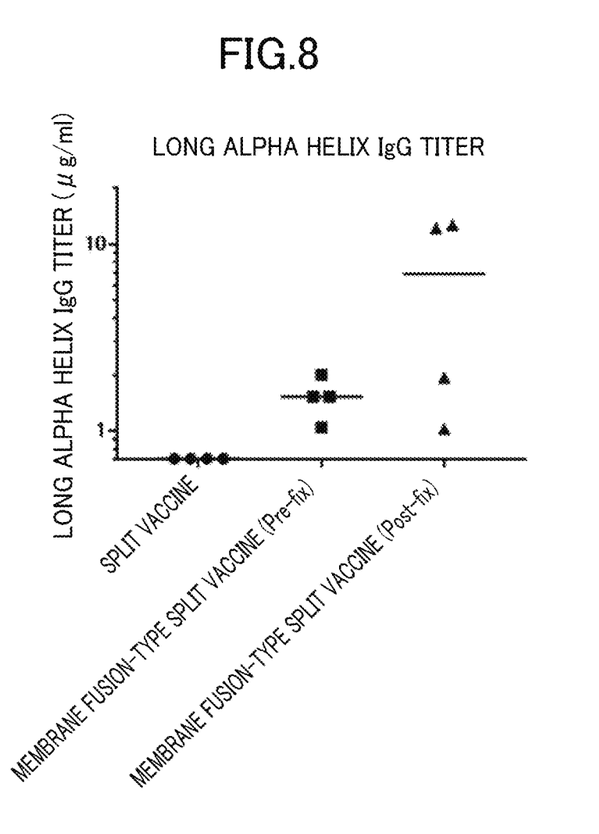
FIG. 8 is a graph showing an increase in the titer of an anti-LAH antibody in sera of mice inoculated with membrane fusion-type H3N2 HA split vaccines ((Pre-fix) and (Post-fix)).

As shown in FIG. 7, the LAH binding monoclonal antibody bound to the vaccine (Post-fix) that had undergone the formalin treatment after the acidic treatment in the process of preparing the membrane fusion-type HA split vaccine more strongly than to the vaccine (Pre-fix) that had undergone the formalin treatment prior to the acidic treatment. The results indicate that when to perform the formalin treatment has influence on the enhancement of the binding capacity of the antibody to the LAH epitope obtained through the acidic treatment of the HA split vaccine, and that the formalin treatment is desirably performed after the acidic treatment. In FIGS. 7 and 8, a membrane fusion-type split vaccine obtained by subjecting the HA split vaccine to the acidic treatment after the formalin treatment in the same manner as described in 8 above is referred to as "(Pre-fix)." Further, according to the procedure of Example 1, a membrane fusion-type split vaccine obtained by subjecting the HA split vaccine to the formalin treatment after the acidic treatment in the same manner as described in Example 1 is referred to as "(Post-fix)."

As shown in FIG. 8, the titer of the anti-LAH antibody in the sera of the BALB/c mice intraperitoneally inoculated with the membrane fusion-type HA split vaccine was higher than the titer of the anti-LAH antibody in the sera of the BALB/c mice intraperitoneally inoculated with the current HA split vaccine. Furthermore, the membrane fusion-type HA split vaccine (Post-fix) exhibited higher titer of the anti-LAH antibody than the membrane fusion-type split vaccine (Pre-fix).

INDUSTRIAL APPLICABILITY

The present invention is useful for the production of influenza vaccines.

[Sequence Listing Free Text]
SEQ ID NO: 1, 2: Synthetic Peptide
[Sequence Listing]

---

The invention claimed is:

1. A method for producing an influenza haemagglutinin (HA) split vaccine which produces an antibody that binds to a long alpha helix (LAH) of a HA stem region, the method comprising:
   treating influenza virus particles with ether to obtain an influenza HA split vaccine; and
   subjecting said influenza HA split vaccine, which has not undergone a formalin treatment, to an acidic treatment.

2. A method for producing an influenza HA split vaccine which produces an antibody that binds to a LAH of a HA stem region, the method comprising:
   treating influenza virus particles with ether to obtain an influenza HA split vaccine; and
   subjecting an influenza HA split vaccine, which has not undergone a formalin treatment, to an acidic treatment, and
   thereafter, subjecting the influenza HA split vaccine to a formalin treatment.

3. A method for producing an influenza HA split vaccine which produces an antibody that binds to a LAH of a HA stem region and which is effective against an influenza virus that causes antigenic variation, the method comprising:
   treating influenza virus particles with ether to obtain an influenza HA split vaccine; and
   subjecting said influenza HA split vaccine, which has not undergone a formalin treatment, to an acidic treatment.

4. The method of claim 1, wherein the acidic treatment is performed at a pH of 4.4 to 5.8.

5. The method of claim 1, wherein the influenza HA split vaccine is of type H3N2 or type H1N1.

6. The method of claim 1, wherein the acidic treatment is performed at a pH of 4.4 to 5.8.

7. The method of claim 2, wherein the acidic treatment is performed at a pH of 4.4 to 5.8.

8. The method of claim 3, wherein the acidic treatment is performed at a pH of 4.4 to 5.8.

9. The method of claim 1, wherein the influenza HA split vaccine is of type H3N2 or type H1N1.

10. The method of claim 2, wherein the influenza HA split vaccine is of type H3N2 or type H1N1.

11. The method of claim 3, wherein the influenza HA split vaccine is of type H3N2 or type H1N1.

12. The method of claim 1, wherein the influenza HA split vaccine is an influenza HA split vaccine of a single HA subtype.

13. The method of claim 2, wherein the influenza HA split vaccine is an influenza HA split vaccine of a single HA subtype.

14. The method of claim 3, wherein the influenza HA split vaccine is an influenza HA split vaccine of a single HA subtype.

15. The method of claim 1, the method including: mixing two or more of influenza HA split vaccine antigens, each of which is produced by subjecting an influenza HA split vaccine of a single subtype to an acidic treatment.

16. The method of claim 2, the method including: mixing two or more of influenza HA split vaccine antigens, each of which is produced by subjecting an influenza HA split vaccine of a single subtype to an acidic treatment.

17. The method of claim 3, the method including: mixing two or more of influenza HA split vaccine antigens, each of which is produced by subjecting an influenza HA split vaccine of a single subtype to an acidic treatment.

18. The method of claim 1, wherein the influenza HA split vaccine which produces an antibody that binds to a LAH of a HA stem region is effective against an influenza virus that causes antigenic variation.

19. The method of claim 2, wherein the influenza HA split vaccine which produces an antibody that binds to a LAH of a HA stem region is effective against an influenza virus that causes antigenic variation.

20. The method of claim 1, wherein said acid treatment changes the structure of the influenza HA split vaccine to a membrane fusion-type HA split vaccine, thus exposing the HA stem region.

21. The method of claim 1, wherein said influenza HA split vaccine produces a LAH binding antibody titer being at least 3-fold higher compared to an influenza HA split vaccine obtained without the acidic treatment.

22. The method of claim 20, wherein said influenza HA split vaccine produces a LAH binding antibody titer being at least 3-fold higher compared to an influenza HA split vaccine obtained without the acidic treatment.

23. The method of claim 2, wherein said acid treatment changes the structure of the influenza HA split vaccine to a membrane fusion-type HA split vaccine, thus exposing the HA stem region.

24. The method of claim 2, wherein said influenza HA split vaccine produces a LAH binding antibody titer being at least 3-fold higher compared to an influenza HA split vaccine obtained without the acidic treatment.

25. The method of claim 23, wherein said influenza HA split vaccine produces a LAH binding antibody titer being at least 3-fold higher compared to an influenza HA split vaccine obtained without the acidic treatment.

26. The method of claim 3, wherein said acid treatment changes the structure of the influenza HA split vaccine to a membrane fusion-type HA split vaccine, thus exposing the HA stem region.

27. The method of claim 3, wherein said influenza HA split vaccine produces a LAH binding antibody titer being at least 3-fold higher compared to an influenza HA split vaccine obtained without the acidic treatment.

28. The method of claim 26, wherein said influenza HA split vaccine produces a LAH binding antibody titer being at least 3-fold higher compared to an influenza HA split vaccine obtained without the acidic treatment.

* * * * *

UNITED STATES PATENT AND TRADEMARK OFFICE
CERTIFICATE OF CORRECTION

PATENT NO. : 11,732,031 B2
APPLICATION NO. : 16/292065
DATED : August 22, 2023
INVENTOR(S) : Yoshimasa Takahashi, Yu Adachi and Manabu Ato It is certified that error appears in the above-identified patent and that said Letters Patent is hereby corrected as shown below:

On the Title Page

Column 2 item (56) (Other Publications), delete "Achimeric" and insert -- A chimeric --.

Column 2 item (57) (Abstract), delete "variation," and insert -- variation. --.

Signed and Sealed this
Twenty-eighth Day of November, 2023

Katherine Kelly Vidal
*Director of the United States Patent and Trademark Office*